US012758679B2

(12) United States Patent
Kim et al.

(10) Patent No.: US 12,758,679 B2
(45) Date of Patent: Oct. 13, 2026

(54) COMPOSITION FOR TREATING WOUND COMPRISING DERMAL TISSUE-DERIVED EXTRACELLULAR MATRIX AND METHOD FOR PREPARING SAME

(71) Applicant: L&C Bio Co., Ltd., Seongnam-si (KR)

(72) Inventors: Sang Chul Kim, Eunpyeong-Gu (KR); Kee Won Lee, Mapo-gu Seoul (KR); Hyung Gu Kim, Nowon-gu Seoul (KR); Whan Chul Lee, Seongdong-gu Seoul (KR)

(73) Assignee: L&C BIO CO., LTD., Gyeonggi-Do (KR)

( * ) Notice: Subject to any disclaimer, the term of this patent is extended or adjusted under 35 U.S.C. 154(b) by 412 days.

(21) Appl. No.: 18/268,590

(22) PCT Filed: Dec. 21, 2020

(86) PCT No.: PCT/KR2020/018770

§ 371 (c)(1),
(2) Date: Jun. 20, 2023

(87) PCT Pub. No.: WO2022/138993

PCT Pub. Date: Jun. 30, 2022

(65) Prior Publication Data

US 2024/0042095 A1 Feb. 8, 2024

(51) Int. Cl.
*A61L 26/00* (2006.01)

(52) U.S. Cl.
CPC ....... *A61L 26/0057* (2013.01); *A61L 26/0023* (2013.01); *A61L 2300/64* (2013.01)

(58) Field of Classification Search
None
See application file for complete search history.

(56) References Cited

U.S. PATENT DOCUMENTS

| | | | |
|---|---|---|---|
| 7,741,116 | B2 | 6/2010 | Boyce |
| 2018/0311399 | A1 | 11/2018 | Park et al. |

FOREIGN PATENT DOCUMENTS

| | | | |
|---|---|---|---|
| JP | 4555576 | B2 | 10/2010 |
| KR | 10-1523878 | B1 | 5/2015 |
| KR | 10-2015-0143311 | A | 12/2015 |
| KR | 10-2016-0049459 | A | 5/2016 |
| KR | 10-1729127 | | 5/2016 |
| KR | 10-1649792 | | 8/2016 |
| WO | 2016010330 | A1 | 1/2016 |

OTHER PUBLICATIONS

Korean International Search Report issued in PCT/KR2020/018770 on Sep. 15, 2021.
Chinese Office Action issued on Mar. 8, 2023, in corresponding Korean Patent Application No. 202080050375.2.

*Primary Examiner* — Michael V Meller
(74) *Attorney, Agent, or Firm* — Panitch Schwarze Belisario & Nadel LLP

(57) ABSTRACT

Disclosed is a composition for treating a wound including a dermis-derived extracellular matrix and a method for preparing the composition. By using the composition for treating a wound according to the present invention, the composition can be applied to wounds of various sizes and depths by increasing the viscosity of the composition, the composition is well coagulated without falling off for a certain period of time after application to a wound surface, and the composition can promote recovery.

9 Claims, 4 Drawing Sheets

[FIG. 1]
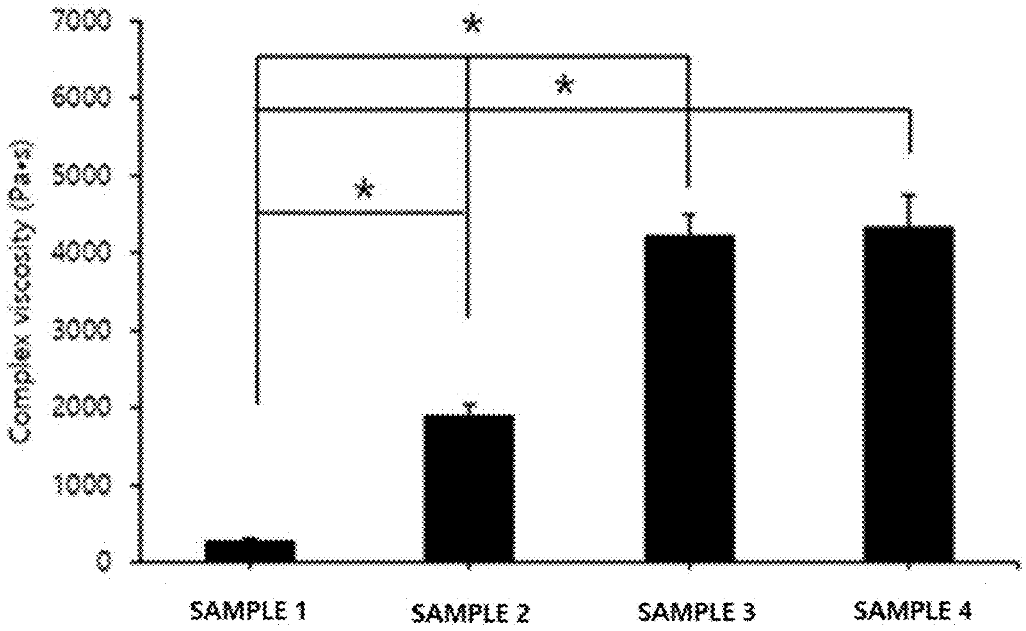
[FIG. 2]
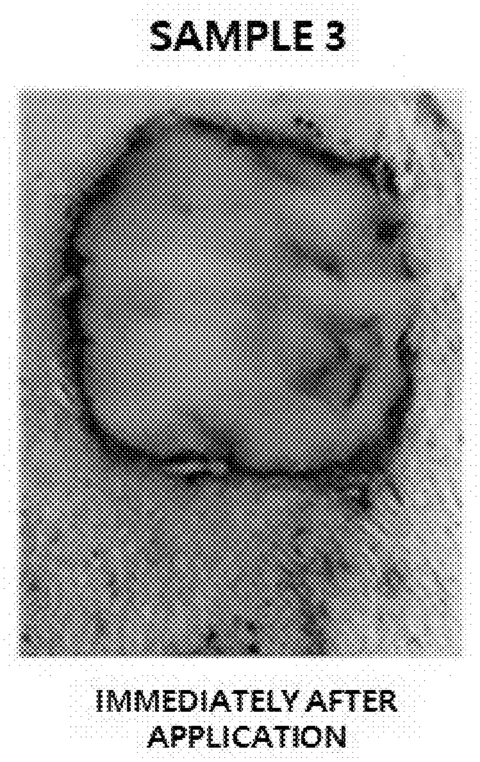

[FIG. 3A]
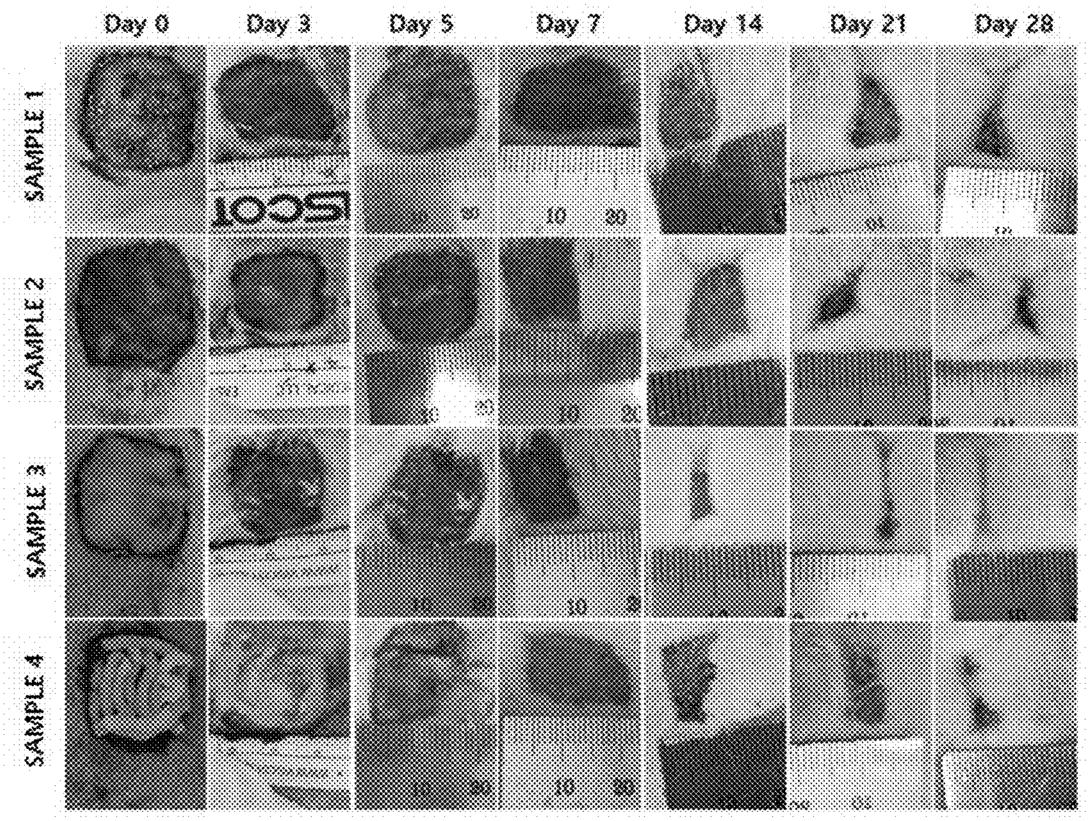
[FIG. 3B]
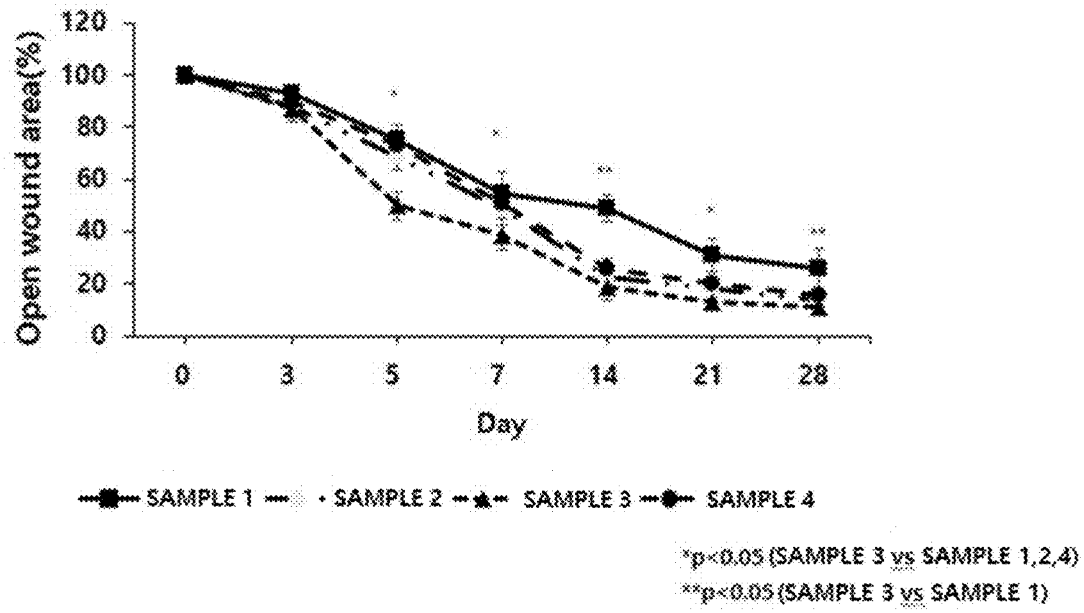

[FIG. 4A]
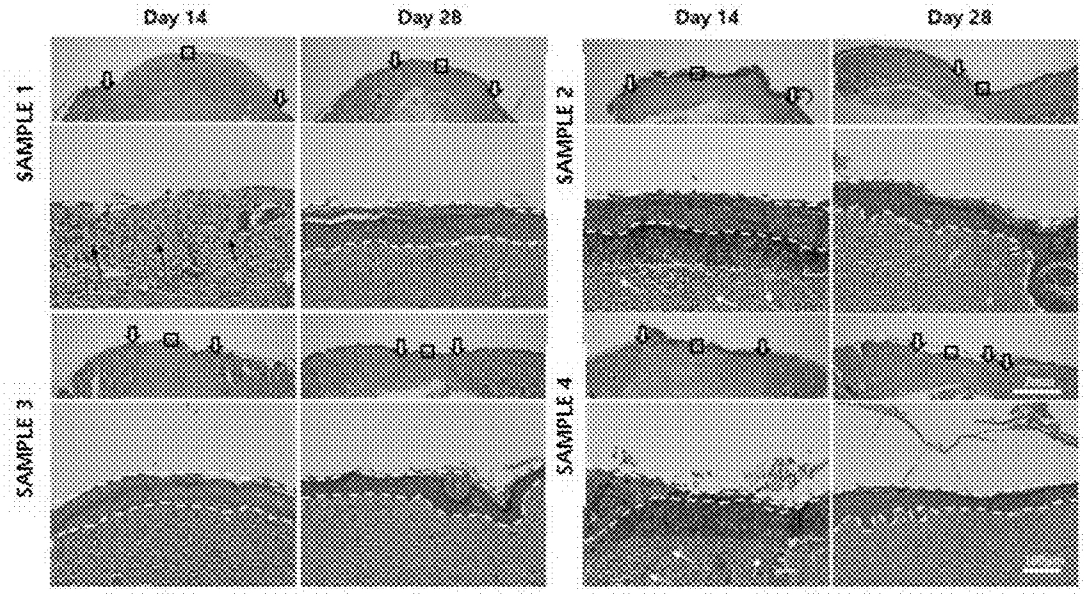
[FIG. 4B]
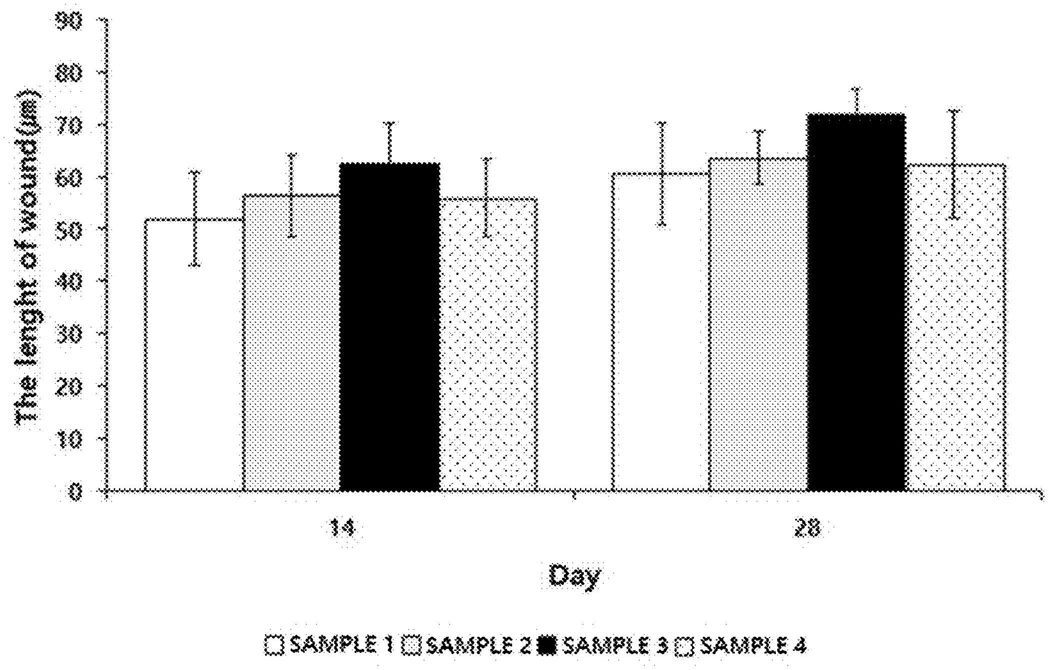

[FIG. 5A]
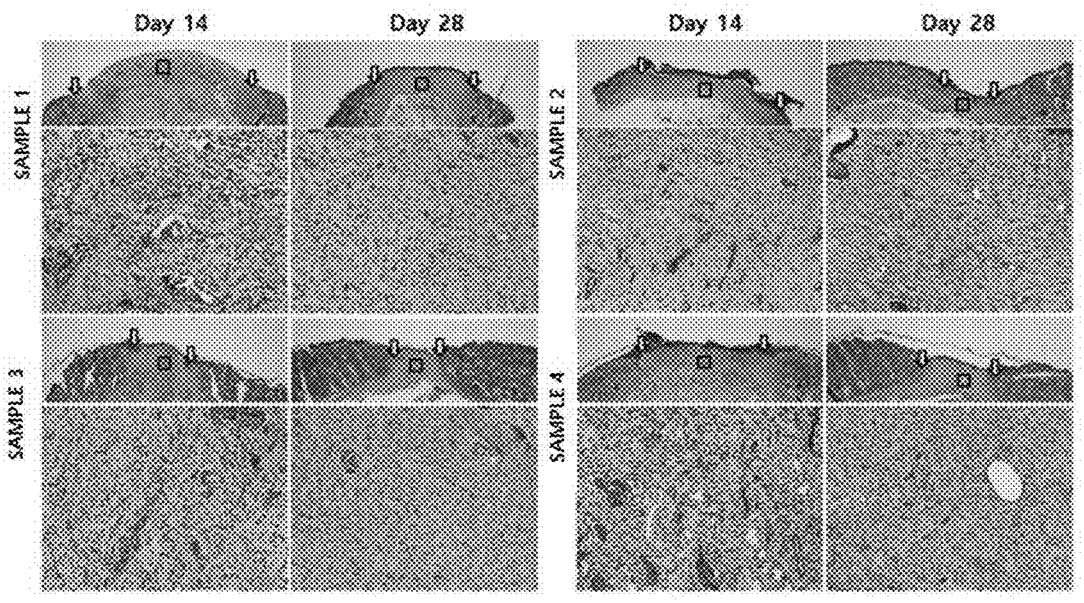
[FIG. 5B]
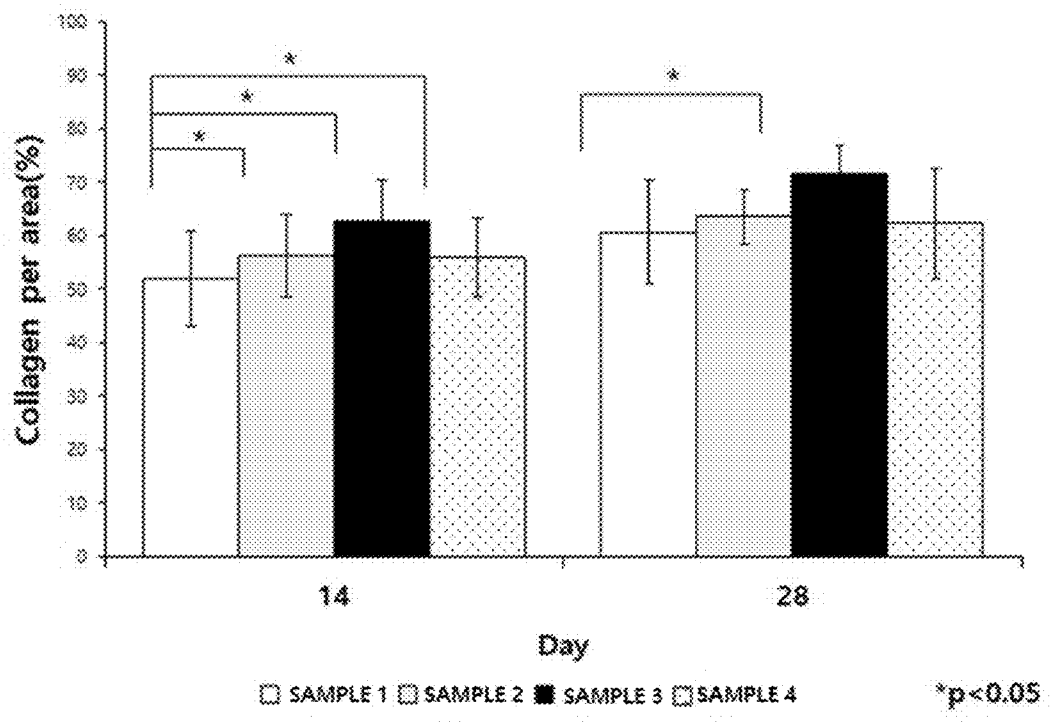

COMPOSITION FOR TREATING WOUND COMPRISING DERMAL TISSUE-DERIVED EXTRACELLULAR MATRIX AND METHOD FOR PREPARING SAME

CROSS-REFERENCE TO RELATED APPLICATIONS

This application is a Section 371 of International Application No. PCT/KR2020/018770, filed Dec. 21, 2020, which was published in the Korean language on Jun. 30, 2022, under International Publication No. WO 2022/138993 A1, the disclosure of which is incorporated herein by reference in their entireties.

TECHNICAL FIELD

The present invention relates to a composition for treating a wound, including a dermal tissue-derived extracellular matrix (ECM), and a method of preparing the same.

BACKGROUND ART

Skin is the body's largest organ and serves as the primary defense against external stimulus and infection risk. A wound is a condition in which the original continuity of normal skin is lost by its damage caused by trauma, burns, or surgical procedures, and thus the skin is exposed to external irritation and the risk of infection and is healed through various complicated physiological processes. Wound healing is divided into hemostasis, inflammation, proliferation, and remodeling, and while a light wound may be naturally healed, a chronic wound, such as a diabetic foot ulcer or pressure sores, is difficult to heal naturally, so there is a need for providing a wound dressing capable of not only protecting a wound but also helping regeneration.

Wound dressings refer to medical supplies used to protect wounds and prevent infection, absorb exudate, and prevent hemorrhage and the loss of a body fluid, and are used in various raw materials and forms depending on the purpose of use. Commercially available wound dressing products have various forms such as a sheet type, a foam type, and a gel type, and are manufactured with various raw materials such as biological materials, synthetic polymers, and antibacterial materials. Since conventionally used wound dressings provide only a regenerative environment that induces self-healing at the wound area, they are effective for light wounds, but are less effective for chronic wounds which are difficult to heal naturally.

To solve such disadvantages, stem cells, allogenic dermis, and heterologous dermis are used for the treatment of a chronic wound, but heterologous dermis is limitedly used due to a problem such as the induction of transplant rejection.

Dermal tissue-derived ECM is made immunologically safe by removing a cell component from the dermis of a donor and is widely used to be developed as products such as AlloDerm® (Lifecell) in the US, MegaDerm® (L&C Bio) in Korea, SureDerm™ (Hans Biomed), and CGCryoDerm™ (CG Bio). Collagen, elastin, and fibronectin contained in the dermal tissue-derived ECM induce the attachment and proliferation of cells and help wound healing. Since conventional dermal tissue-derived ECM products are manufactured in a sheet form and are not easily applied to wounds of various sizes and depths, to solve this, it has been reported that dermal tissue-derived ECM is manufactured in a micronized form and then applied for foot ulcers, exhibiting an effect on wounds of various sizes and depths. However, when a wound dressing is manufactured using micronized, dermal tissue-derived ECM as a single component, it is easily detached when applied to the wound surface and thus has the disadvantage of reduced functions as a wound dressing.

Therefore, to solve the disadvantages of the conventional dermal tissue-derived ECM-based wound dressings, the present invention is directed to providing a composition for treating wounds, which cannot be only applied to wounds of various sizes and depths but also not be detached for a predetermined period in an aggregated state even after being applied to a wound surface, and a method of preparing the same.

RELATED ART DOCUMENT

[Patent Document]

1. Korean Patent No. 10-1523878

DISCLOSURE

Technical Problems

The present invention is directed to providing a composition for treating wounds, which includes dermal extracellular matrix (ECM), and a method of preparing the same, and more particularly, to a composition for treating wounds prepared by crosslinking delipidated and decellularized dermal ECM with a first biopolymer, and physically mixing the resulting mixture with a second biopolymer, and a method of preparing the same.

The present invention is also directed to providing a composition for treating wounds, which is able to be applied to wounds of various sizes and depths by enhancing the viscosity of the composition, is not detached for a predetermined period while being well aggregated even after being applied to a wound surface, and promotes recovery, and a method of preparing the composition.

Technical Solution

The present invention provides a composition for treating wounds, which includes a crosslinked dermal ECM-first biopolymer product; and a second biopolymer.

In addition, the present invention provides a method of preparing a composition for treating wounds, which includes mixing a crosslinked dermal ECM-first biopolymer product; and a second biopolymer.

Advantageous Effect

A composition for treating wounds, which includes dermal extracellular matrix (ECM), according to the present invention can be applied to wounds of various sizes and depths, cannot be detached for a predetermined period while being well aggregated even after being applied to a wound surface, and can promote recovery.

DESCRIPTION OF DRAWINGS

FIG. 1 is a graph that shows the result of a viscosity test performed according to the mixing ratio of a crosslinked dermal extracellular matrix (ECM)-first biopolymer product and a second biopolymer.

FIG. 2 is an image that confirms a composition for treating wounds not detached when a composition for treating wounds is applied to a wound surface.

FIG. 3 shows the result of analyzing a wound therapeutic effect according to a mixing ratio of a crosslinked dermal ECM-first biopolymer product and a second biopolymer. Specifically, FIG. 3 shows a set of images (A) and a graph (B), which are obtained by observing wound models prepared using rats for 4 weeks after applying a composition for treating wounds, and measuring the size of a wound.

FIG. 4 shows a result of evaluating wound treatment according to a mixing ratio of a crosslinked dermal ECM-first biopolymer product and a second biopolymer in a histological step. Specifically, FIG. 4 shows a set of images (A) of wound areas stained with hematoxylin and eosin (H&E) and a graph (B) obtained by measuring the length of a wound area, when wound models were prepared using rats, a composition for treating wounds was applied thereto, and 2 and 4 weeks later, the rat models were sacrificed.

FIG. 5 shows a result of evaluating collagen density according to a mixing ratio of a crosslinked dermal ECM-first biopolymer product and a second biopolymer. Specifically, FIG. 5 shows a set of images (A) of wound areas stained with Masson's trichrome (MT) and a graph (B) obtained by measuring collagen density, when wound models were prepared using rats, a composition for treating wounds was applied thereto, and 2 and 4 weeks later, the rat models were sacrificed.

MODES OF THE INVENTION

The present invention relates to a composition for treating wounds, which includes a crosslinked dermal extracellular matrix (ECM)-first biopolymer product; and a second biopolymer.

In an embodiment of the present invention, it was confirmed that the composition for treating wounds according to the present invention has an excellent viscoelastic property. In addition, an in vivo experiment was conducted on a composition for treating wounds, confirming that the composition for treating wounds is not detached from a wound area since being well aggregated immediately after being applied to the wound area, has an excellent wound healing effect, and has an excellent collagen production effect.

Hereinafter, the composition for treating wounds according to the present invention will be described in further detail.

The composition for treating wounds of the present invention includes a crosslinked dermal ECM-first biopolymer product, and a second biopolymer.

In the present invention, the crosslinked dermal ECM-first biopolymer product means a complex in which dermal ECM and a first biopolymer are chemically crosslinked.

In the present invention, dermal ECM (hereinafter, referred to as ECM) is known as a material for treating wounds, and collagen, elastin, and fibronectin, contained in the ECM, may induce cell attachment and proliferation and thus exhibit a wound healing effect.

In one embodiment, the ECM refers to a complicated aggregate of biopolymers, filling tissue or extracellular space. The ECM may have different components according to a cell type or the degree of cell differentiation, and consist of a fibrous protein such as collagen or elastin, a complex protein of a proteoglycan or a glycosaminoglycan, and a cell-adhesive glycoprotein such as fibronectin or laminin.

In one embodiment, the dermis may be allogenic or heterologous dermal tissue. The allogenic species may be humans, and the heterologous species may be animals except humans, that is, mammals such as pigs, cows, horses, etc.

In one embodiment, the ECM may be delipidated and decellularized skin-derived dermal tissue. An acellular dermis product that is commercially available as the ECM may be used, or directly manufactured. The manufacture of such ECM will be described in detail in the method of preparing a composition for treating wounds below.

In the present invention, since a first biopolymer is chemically crosslinked with the extracellular matrix (ECM), it is able to lower a degradation rate and remain on a wound area for a long time when the composition for treating wounds according to the present invention is applied to the wound area, thereby increasing a wound healing effect.

In one embodiment, the type of first biopolymer is not particularly limited, and may include one or more selected from the group consisting of collagen, hyaluronic acid, chitosan, carboxymethylcellulose, alginate, gelatin, and hydroxyapatite.

In one embodiment, the first biopolymer may be hyaluronic acid.

The "hyaluronic acid" is a biosynthetic natural substance abundant in the skin, joint fluid, cartilage, etc. of an animal, and is a hydrophilic mucopolysaccharide because of a large amount of hydroxide groups. The hyaluronic acid is coupled with water to be formed into a gel and is involved in the lubricating action of joints or the flexibility of the skin, and plays an important role for preventing bacterial invasion or the skin penetration of a toxin due to high viscosity. Such hyaluronic acid shows a difference between a physical property and a physiological property due to crosslinking through a physical method such as UV, radiation, and electron beams, or a chemical method using BDDE.

The first biopolymer may have a molecular weight of 10 to 2,000 kDa.

In the present invention, the ECM and the first biopolymer form crosslinking by a crosslinking agent. Specifically, the ECM and the first biopolymer may form a linkage by a crosslinking agent.

In one embodiment, a multifunctional compound may be used as the crosslinking agent. In the multifunctional compound, binding of an amine group ($-NH_2$), a hydroxyl group (—OH), or a thiol group (—SH) of the ECM to one functional group may be formed, or binding of a hydroxyl group of hyaluronic acid may bind to another functional group.

In one embodiment, the average particle diameter of the crosslinked ECM-first biopolymer product may vary according to the size and depth of an applied area, that is, a wound, and may be, for example, 100 to 800 μm. Within the particle diameter range, the crosslinked product can be applied to wound areas of various shapes and depths.

In one embodiment, the content of the crosslinked ECM-first biopolymer product may be 5 to 40 parts by weight, 15 to 40 parts by weight, 15 to 30 parts by weight, or 15 to 25 parts by weight with respect to the total weight of the composition. In this range, the crosslinked product may exhibit an excellent wound healing effect. When the content of the crosslinked product exceeds 40 parts by weight, it does not show a significant wound healing effect and rather partially reduces a healing effect, so it is preferable to adjust the content range to be 5 to 40 parts by weight.

In the present invention, a second biopolymer may enhance the viscoelastic property of the composition for treating wounds and enhance an adhesion strength at a wound site, thereby preventing detachment of the composition for treating wounds.

Such a second biopolymer may be non-crosslinked, or chemically-crosslinked one or more biopolymers, that is, a crosslinked biopolymer product.

In one embodiment, the second biopolymer may have a molecular weight of kDa to 2,000 kDa.

In one embodiment, as the second biopolymer, one or more selected from the group consisting of collagen, hyaluronic acid, chitosan, carboxymethylcellulose, alginate, gelatin, and hydroxyapatite may be used.

In addition, as the second biopolymer, a crosslinked product of one or more biopolymers selected from the group consisting of collagen, hyaluronic acid, chitosan, carboxymethylcellulose, alginate, gelatin, and hydroxyapatite may be used.

In one embodiment, as the second biopolymer, a polymer that is identical to the first biopolymer may be used.

In one embodiment, in the crosslinked biopolymer product, the biopolymers may be crosslinked by a crosslinking agent, and as the crosslinking agent, a multifunctional compound may be used.

In one embodiment, the content of the second biopolymer may be 60 to 95 parts by weight, 60 to 85 parts by weight, 70 to 85 parts by weight, or 75 to 85 parts by weight with respect to the total weight of the composition. Within the above range, the physical properties of the composition for treating wounds may be enhanced.

In the present invention, the complex viscosity of the composition for treating wounds may be 1,000 to 10,000 Pa·s. The complex viscosity refers to a result value measured by a rotational rheometer analyzer (frequency: 0.1~10 Hz, temperature: 25° C., strain: 1%).

Viscoelasticity refers to a phenomenon in which the properties of a liquid and the properties of a solid appear simultaneously when a force is applied to a material. In the present invention, a viscous modulus, a modulus, and a complex viscosity may be measured by measuring a force that the composition is resistant to an applied force and a lost force.

A viscous modulus (G") refers to a viscous component of material as a measure of lost energy. Elastic modulus (storage modulus, G') refers to the ratio of stress and strain of an elastic body within its elastic limit. As the modulus increases, the composition becomes harder and is highly resistant to strain. The complex viscosity is a frequency-dependent viscosity calculated by a method of measuring a frequency, and is a value that reflects G", G', and a measured frequency value. Such complex viscosity may be, specifically, 3,000 to 6,000 Pa·s.

In one embodiment, the composition for treating wounds of the present invention may be applied to a wound area.

The composition for treating wounds according to the present invention is able to be applied to wounds of various sizes and depths by enhancing the viscosity of the composition, may not be detached for a predetermined period while being well aggregated even after being applied to a wound surface, and may promote recovery.

In addition, the present invention relates to a method of preparing the composition for treating wounds described above.

The method of preparing the composition for treating wounds may include mixing a crosslinked ECM-first biopolymer product; and a second biopolymer.

In the present invention, the crosslinked ECM-first biopolymer product may be prepared by a) removing a lipid component from skin tissue;

b) preparing ECM by removing cells from adipose tissue from which the lipid component is removed;

c) freeze-drying the adipose tissue from which cells are removed;

d) powdering the freeze-dried lyophilisate;

e) preparing a crosslinked ECM-first biopolymer product by crosslinking the powdered ECM and the first biopolymer;

f) freeze-drying the crosslinked ECM-first biopolymer product; and g) powdering the freeze-dried lyophilisate.

In the present invention, the ECM may be commercially available or prepared in vitro.

In the present invention, washing may be performed before a). In washing, skin tissue may be washed with sterile distilled water. Through this step, impurities in the skin tissue may be removed.

In addition, the present invention may further include removing the epidermis and purple spots from skin tissue. This step may be performed before a), or performed before chemical treatment following physical treatment in a), which will be described below.

In one embodiment, this step may be performed using sodium chloride and/or hydrogen peroxide.

In the present invention, a) is a step of removing a lipid component from skin tissue as a delipidation step.

In one embodiment, delipidation refers to removing a lipid component from tissue.

In one embodiment, the removal of a lipid component may be performed by physical or chemical treatment, or by both treatments. When both treatments are performed, chemical treatment following physical treatment may be performed.

In one embodiment, the type of physical treatment is not particularly limited, and the physical treatment may be performed using grinding. The grinding may be performed using a grinding means known in the art, for example, a mixer, a homogenizer, a freezing mill, an ultrasonic mill, a hand blender, or a plunger mill.

In one embodiment, the type of chemical treatment is not particularly limited, and the chemical treatment may be performed using a delipidation solution. The delipidation solution may include a polar solvent, a non-polar solvent, or a mixed solvent thereof. As the polar solvent, water, an alcohol or a mixed solution thereof may be used, and as an alcohol, methanol, ethanol, or isopropyl alcohol may be used.

In addition, as a non-polar solvent, hexane, heptane, octane, or a mixed solution thereof may be used. Specifically, in the present invention, as the delipidation solution, a mixed solution of isopropyl alcohol (IPA) and hexane may be used. Here, the mixing ratio of the isopropyl alcohol and the hexane may be 20:80 to 80:20.

The treatment time of the delipidation solution may be 1 to 8 hours.

In the present invention, b) is a decellularization step, which is to remove cells from skin tissue from which a lipid component is removed in a).

In one embodiment, decellularization means the removal of cell components except the ECM, for example, a nucleus, a cell membrane, and a nucleic acid, from tissue.

This step may be performed using a decellularization solution, and as a decellularization solution, one or more selected from the group consisting of sodium hydroxide, potassium hydroxide, ammonium hydroxide, calcium carbonate, magnesium hydroxide, calcium hydroxide, ammonia, sodium deoxycholate (SDC) and sodium dodecyl sulfate (SDS), alkylbenzene sulfonate (ALS), alcohol ether sulfates (AES), sodium lauryl sulfate (SLS), and polyethylene glycol (PEG) may be used.

In one embodiment, the concentration of the decellularization solution may be 0.1 to 10%. In the above concentration range, it is easy to remove cells.

In addition, in one embodiment, the decellularization step may be performed for 30 minutes to 10 hours. Within the above time range, it is easy to remove cells.

In the present invention, the skin tissue that has undergone decellularization may be expressed as ECM.

In the present invention, after b), washing may be further performed. By washing, impurities in a) delipidation and b) decellularization may be removed, and high purity of ECM may be obtained.

In the present invention, c) is a freeze-drying step, which is a step of freeze-drying the resulting product of the above-described step, that is, b). The freeze-drying is a method of absorbing moisture in vacuo after rapid cooling while the tissue is frozen, and this method can control moisture in the ECM material through freeze-drying, and facilitate powdering.

In one embodiment, freeze-drying may be performed at −50 to −80° C. for 24 to 96 hours.

In one embodiment, the moisture content of the freeze-dried ECM may be 10% or less or 1 to 8%.

In the present invention, d) is a powdering step for powdering a freeze-dried lyophilisate, that is, ECM.

The powdered ECM may have a particle diameter of 100 to 800 μm.

In the present invention, e) is a crosslinking step for preparing a crosslinked ECM-first biopolymer product by crosslinking the powdered ECM and the first biopolymer.

In one embodiment, for the first biopolymer, the above-described component may be used without limitation, and specifically, hyaluronic acid may be used.

In one embodiment, the content of hyaluronic acid may be 1 to 1,000 parts by weight, or 5 to 1,000 parts by weight with respect to 100 parts by weight of the ECM. Within the content range, the biopolymer may primarily form a cross-link with the ECM, and prevent degradation of the ECM in a wound area. When the content of hyaluronic acid exceeds 1,000 parts by weight, a high concentration of hyaluronic acid may bind to the ECM, thereby reversing the major physical properties of the crosslinked product to the physical properties of hyaluronic acid, rather than the physical properties of the dermis, so the content of hyaluronic acid is preferably used within the above range.

In one embodiment, crosslinking may be performed in the presence of a crosslinking agent. As the crosslinking agent, a multifunctional compound may be used, and specifically, one or more selected from the group consisting of 1,4-butandiol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, and sorbitol polyglycidyl ether may be used.

In one embodiment, the content of the crosslinking agent may be 0.5 to 10 parts by weight with respect to the content of the ECM.

In one embodiment, the crosslinking time may be 1 to 5 hours.

According to e), a crosslinked ECM-first biopolymer product is prepared.

In the present invention, after e), washing may be further performed. The washing may be performed through centrifugation.

In the present invention, f) is a freeze-drying step for freeze-drying the crosslinked ECM-first biopolymer product.

Through the freeze-drying, moisture in the crosslinked product may be adjusted, and powdering may be easily performed.

In one embodiment, the freeze-drying may be performed at −50 to −80° C. for 24 to 96 hours.

In one embodiment, the content of moisture in the freeze-dried crosslinked product may be 10% or 1 to 8%.

In the present invention, g) is a powdering step for powdering the freeze-dried lyophilisate.

The powdered, crosslinked ECM-first biopolymer product may have a particle diameter of 100 to 800 μm.

In the present invention, the second biopolymer may be a commercially available product. In addition, when the crosslinked biopolymer product is used as the second biopolymer, the crosslinked product may be prepared by crosslinking a biopolymer using a crosslinking agent; and drying the crosslinked product.

In the present invention, in the crosslinking step, the biopolymer may be crosslinked using a crosslinking agent. As the biopolymer and the crosslinking agent, the above-described first biopolymer and crosslinking agent may be used without limitation.

In one embodiment, the content of the crosslinking agent may be 0.5 to 10 parts by weight, relative to the biopolymer.

In the present invention, the drying step may be a step for drying the biopolymer crosslinked by crosslinking, wherein the crosslinked product may be prepared in the form of a carrier by dialyzing the biopolymer and drying it with hot wind.

In one embodiment, in the prepared carrier, the content of the biopolymer may be 1 to 10%.

In the present invention, the crosslinked ECM-first biopolymer product; and a second biopolymer may be mixed by physical mixing.

In one embodiment, the content of the crosslinked ECM-first biopolymer product in the mixture may be 5 to 40 parts by weight, 15 to 40 parts by weight, 15 to parts by weight, or 15 to 25 parts by weight.

In addition, the content of the second biopolymer in the mixture may be 60 to 95 parts by weight, 60 to 85 parts by weight, 70 to 85 parts by weight, or 75 to 85 parts by weight.

In one embodiment, when a non-crosslinked biopolymer is used as a second biopolymer, a polymer solution including 1 to 10% of the biopolymer may be used. In addition, when the polymer solution is used in the form of the above-described carrier, the content of the biopolymer in the carrier may be 1 to 10%.

In one embodiment, a mixture may be prepared by mixing the crosslinked ECM-first biopolymer product and the second biopolymer.

The present invention may further include sterilizing the mixture.

According to sterilization, the immunity in the composition for treating wounds may be removed, and bacteria or the like may be effectively disrupted.

In one embodiment, the sterilization may be performed by UV irradiation, and a UV irradiation range may be 10 to 30 kGy.

The present invention will be described in further detail with reference to the following examples. However, the scope of the present invention is not limited to the following examples, and it will be understood by those of ordinary skill in the art that various modifications, alterations, or applications are possible without departing from the technical details derived from the details described in the accompanying claims.

EXAMPLES

Example 1. Preparation of Composition for Treating Wounds (1) Preparation of Micronized, Crosslinked ECM-First Biopolymer Product ① Preparation of Micronized ECM Skin tissues (collected from cadavers donated by a tissue bank for non-profit patient treatment) were prepared.

Skin tissue was washed with sterile distilled water. From the washed skin tissue, fascia and lipids were physically removed using scissors. The skin tissue was treated with 0.1 to 10M sodium chloride and 1 to 10% hydrogen peroxide for 24 hours to remove the epidermis and purple spots from the skin tissue. For the epidermis- and purple spot-removed skin tissue, 40 to 60% isopropyl alcohol and 40 to 60% hexane were used to perform delipidation for 2 hours. For the lipid-removed skin tissue, a 0.1 to 10% SDS solution was treated to remove cells (preparation of ECM).

The prepared ECM was washed with sterile distilled water for 2 hours. The ECM was freeze-dried to adjust the moisture content to be 10% or less. The freeze-dried ECM was micronized using a micro grinder.

② Preparation of micronized, crosslinked ECM-first biopolymer product

A crosslinked ECM-hyaluronic acid product was prepared by mixing micronized ECM and hyaluronic acid (HA) with 1,4-butanediol diglycidyl ether (BDDE) as a crosslinking agent.

Specifically, a reaction solvent was prepared by adding 1 to 10 mL of BDDE per 100 mL of 0.1N to 1N sodium hydroxide aqueous solution. A mixed solution was prepared by adding 1 to 20 g of HA and 1 to 20 g of the micronized ECM to the prepared reaction solvent and mixing them homogeneously.

The mixed solution was reacted at 30 to 50° C. for 3 hours to complete crosslinking. A supernatant was removed by centrifuging the crosslinked reaction product at 8,000 rpm for 10 minutes, and washing was repeated 5 to 10 times.

A moisture content was adjusted to 10% or less by freeze-drying the micronized, crosslinked ECM-hyaluronic acid product. The freeze-dried, micronized, crosslinked ECM-hyaluronic acid product was micronized using a micro grinder. The prepared crosslinked ECM-hyaluronic acid product had a particle size of 100 to 800 μm.

(2) Preparation of Second Biopolymer (HA Carrier)

A hyaluronic acid (HA) carrier was prepared by mixing HA with 1,4-butanediol diglycidyl ether (BDDE) as a crosslinking agent.

Specifically, a reaction solvent was prepared by adding 1 to 10 mL of BDDE per 100 mL of 0.1N to 1N sodium hydroxide aqueous solution. A mixed solution was prepared by adding 1 to 20 g of HA to the prepared reaction solvent and mixing them homogeneously. The mixed solution was reacted at 50° C. for 3 hours to complete crosslinking.

The crosslinked reaction product was added to a dialysis membrane and dialyzed against 5 L of phosphate-buffered saline at room temperature. After 2 hours, the solution was changed with 5 L of 50% EtOH and dialyzed at room temperature for 1 hour. Afterward, an HA carrier was obtained by dialysis against sterile distilled water at room temperature for 72 hours.

(3) Preparation of Composition for Treating Wounds

The micronized, crosslinked ECM-HA product prepared in (1) and the HA carrier prepared in (2) were mixed in the contents shown in the following table, and then the final mixed product was sterilized with 25 kGy gamma radiation.

TABLE 1

| Sample No. | Micronized, crosslinked ECM-biopolymer product | HA carrier |
|---|---|---|
| 1 | 0 | 100 |
| 2 | 10 | 90 |
| 3 | 20 | 80 |
| 4 | 30 | 70 |

Experimental Example 1. Analysis of Physical Properties of Composition for Treating Wounds (1) Viscosity Analysis The viscosities of the compositions for treating wounds prepared in Example 1 (Samples 1 to 4) were confirmed.

Specifically, complex viscosities were measured on Samples 1 to 4 using a rotary rheometer (analysis conditions: frequency=0.1~10 Hz, temperature=25° C., strain=1%).

The measurement result is shown in FIG. 1.

As shown in FIG. 1, the complex viscosity of Sample 1 consisting of only an HA carrier was measured to be 280 Pa·s, the complex viscosity of Sample 2 including both components was measured to be 1,890 Pa·s, the complex viscosity of Sample 3 was measured to be 4,210 Pa·s, and the complex viscosity of Sample 4 was measured to be 4,340 Pa·s. From the above result, it can be confirmed that the complex viscosities of Samples 3 and 4 are significantly higher than those of Samples 1 and 2.

In other words, when the micronized, crosslinked ECM-HA product is included at 20% or more, it can be confirmed that it has an excellent complex viscosity value.

Experimental Example 2. Verification of In Vivo Performance of a Composition for Treating Wounds To verify the performance of the compositions for treating wounds prepared in Example 1 (Samples 1 to 4), an animal test was conducted.

Specifically, to adjust wounds of large sizes and depths, full-thickness wounds in a square shape (W×L×D: 2 cm*2 cm*0.5 cm) were induced to the dorsal area of SD rats, and 0.5 cc of each sample was applied to a wound area. The results were analyzed by sacrificing the experimental animals at Week 2 and Week 4 after application.

(1) Verification of Shape Retention Immediately after Application of Composition for Treating Wounds An image was photographed immediately after the application of a composition for treating wounds.

FIG. 2 is the image obtained by photographing a wound area immediately after the application of Sample 3 to the wound surface. As shown in FIG. 2, it can be confirmed that the composition for treating wounds is well agglomerated and is not detached from the wound area.

(2) Verification of Wound Healing Effect

Changes in wound areas for 4 weeks after the application of compositions for treating wounds were photographed, and the areas of the wound areas were measured using digital calipers.

FIG. 3 shows (A) images obtained by photographing changes in wound areas for 4 weeks and (B) the result of measuring the areas of the wound areas.

As shown in FIG. 3, it can be confirmed that, in the case of Sample 3, compared with Samples 1, 2, and 4, a higher wound healing effect is exhibited. Particularly, it can be confirmed that, in the case of Sample 3, compared with Samples 1, 2, and 4, a wound size is significantly reduced from day 5.

(3) Wound Healing Analysis

Wound areas were extracted by sacrificing the experimental animals at week 2 and week 4 after the application of compositions for treating wounds. The extracted wound areas were fixed with 10% formalin to form paraffin blocks, and then slides were manufactured using a freezing microtome. The slide of each sample was stained with H&E to perform tissue analysis, and the wound healing effect was confirmed by measuring the length of a wound area.

FIG. 4 shows the result of confirming a wound healing effect.

As shown in FIG. 4, as a result of H&E staining, it can be confirmed that, in the case of Sample 3, the length of a wound area is rapidly reduced over time, compared with Samples 1, 2, and 4.

(4) Evaluation of Collagen Density

Collagen production at the wound area extracted in (3) was confirmed.

Specifically, the slide of each sample was stained with MT to perform tissue analysis, and collagen density was evaluated.

FIG. 5 shows the result of measuring collagen density.

As shown in FIG. 5, as a result of MT staining, it can be confirmed that, in the case of Sample 3, collagen production is higher than those of Samples 1, 2, and 4.

INDUSTRIAL APPLICABILITY

A composition for treating wounds, including dermal extracellular matrix (ECM), according to the present invention cannot only be applied to wounds of various sizes and depths but also promote recovery without detachment for a predetermined period while the composition is well agglomerated even after application.

The invention claimed is:

1. A composition for treating wounds consisting essentially of:

a first biopolymer crosslinked to a dermal extracellular matrix (ECM); and a second biopolymer; wherein:

the first biopolymer is selected from the group consisting of collagen, hyaluronic acid, chitosan, carboxymethylcellulose, alginate, gelatin, and hydroxyapatite;

the second biopolymer is selected from the group consisting of collagen, hyaluronic acid, chitosan, carboxymethylcellulose, alginate, gelatin, and hydroxyapatite, or the second biopolymer is a crosslinked product of a biopolymer selected from the group consisting of collagen, hyaluronic acid, chitosan, carboxymethylcellulose, alginate, gelatin, and hydroxyapatite;

the content of the first biopolymer crosslinked to a dermal extracellular matrix is 5 parts to 40 parts by weight with respect to the total weight of the composition, and the composition for treating wounds has a complex viscosity of 1,000 Pa S to 10,000 Pa S;

wherein the first biopolymer crosslinked to a dermal extracellular matrix is prepared by:

i) removing a lipid component from skin tissue of a human;

ii) preparing dermal ECM by removing cells from adipose tissue from which the lipid component is removed;

iii) freeze-drying the adipose tissue from which cells are removed;

iv) powdering the freeze-dried lyophilizate;

v) preparing a first biopolymer crosslinked to a dermal extracellular matrix by crosslinking the powdered dermal ECM and the first biopolymer;

vi) freeze-drying the crosslinked dermal ECM-first biopolymer product; and vii) powdering the freeze-dried lyophilizate;

viii) preparing the second biopolymer by crosslinking the biopolymer using a crosslinking agent; and drying the resulting crosslinked product, wherein the crosslinking agent of the first biopolymer and the second biopolymer is selected from the group consisting of 1,4-butandiol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy) ethylene, pentaerythritol polyglycidyl ether, and sorbitol polyglycidyl ether; and ix) mixing the crosslinked dermal extracellular matrix (ECM)-first biopolymer product and the second crosslinked biopolymer.

2. The composition of claim 1, wherein the dermal ECM is delipidated and decellularized skin-derived dermal tissue.

3. The composition of claim 1, wherein the crosslinked dermal ECM-biopolymer product has an average particle diameter of 100 to 800 μm.

4. The composition of claim 1, wherein the content of the second biopolymer is 60 parts to 95 parts by weight with respect to the total weight of the composition.

5. The composition of claim 1, wherein i) is performed using a delipidation solution, and the delipidation solution is a polar solvent, a non-polar solvent, or a mixed solvent thereof.

6. The composition of claim 1, wherein ii) is performed using a decellularization solution, and the decellularization solution consists essentially of a salt selected from the group consisting of sodium hydroxide, potassium hydroxide, ammonium hydroxide, calcium carbonate, magnesium hydroxide, calcium hydroxide, ammonia, sodium deoxycholate (SDC), sodium dodecyl sulfate (SDS), alkylbenzene sulfonate (ALS), alcohol ether sulfates (AES), sodium lauryl sulfate (SLS), and polyethylene glycol (PEG).

7. The composition of claim 1, wherein v) is performed in the presence of a crosslinking agent, and the crosslinking agent is selected from the group consisting of 1,4-butandiol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, and sorbitol polyglycidyl ether.

8. The composition of claim 7, wherein the content of the crosslinking agent is 0.5 to 10 parts by weight with respect to the weight of the dermal ECM.

9. The composition of claim 1, further consisting essentially of sterilizing the resulting mixture of the crosslinked dermal extracellular matrix (ECM)-first biopolymer product and the second crosslinked biopolymer.

* * * * *